United States Patent [19]

Baum et al.

[11] Patent Number: 5,023,360

[45] Date of Patent: Jun. 11, 1991

[54] SIMPLIFIED SYNTHESIS OF DIALKYLGOLD(III) BETA-DIKETONATES

[75] Inventors: Thomas H. Baum, San Jose; Phillip J. Brock, Sunnyvale; Daniel J. Dawson, San Jose, all of Calif.

[73] Assignee: International Business Machines Corporation, Armonk, N.Y.

[21] Appl. No.: 517,272

[22] Filed: May 1, 1990

[51] Int. Cl.$^5$ ............................................. C07F 1/12
[52] U.S. Cl. .................................. 556/117; 556/110; 556/112; 556/113
[58] Field of Search ....................... 556/110, 112, 113

[56] References Cited

PUBLICATIONS

Gilman, H. and Woods, L. A. "Trimethylgold." Journal of American Chemical Society; vol. 70, pp. 550-52 (1948).
Chemical Abstracts, vol. 93, No. 11; Sep. 15, 1980, p. 747, Abstract No. 114651p.
Zharkova, G. I.; Igremenov, I. K.; Zemskov, S. V., "Chelates of dimethylgold (III) with p-diketones." Koord Khim (Sov J Coord Chem.) 6th 1980 pages 720-23.
Zharkova et al. "Chelates of Dimethylgold(III) with beta-Diketones" in Russian J. Chem. Soc. 762-67 (1939) Brain et al. "The Organic Compounds of Gold" Part VII; Methyl and Ethyl Compounds.
J. A. Chem. Soc. 99, pp. 3695-3703 (1977). Komiya et al. "Reversible Linkage by Isomerisms of beta-Dikenato Ligands. Oxygen-Bonded and Carbon-Bonded Structures in Gold(III) Acetylacetonate Complexes Induced by Phosphines".

Primary Examiner—Arthur C. Prescott
Assistant Examiner—Porfirio Nazario
Attorney, Agent, or Firm—John A. Stemwedel

[57] ABSTRACT

Dialkyl gold(III) $\beta$-diketonates are synthesized in a two-step, one-pot process using a gold trihalide, an alkyl lithium compound and a $\beta$-diketone.

5 Claims, No Drawings

SIMPLIFIED SYNTHESIS OF DIALKYLGOLD(III) BETA-DIKETONATES

DESCRIPTION

1. Field of Invention

The invention of this application relates to a process for the synthesis of dialkylgold(III) β-diketonates. The synthesized compounds, especially dimethylgold(III) trifluoroacetylacetonate, are particularly useful in laser induced metallization of semiconductor components. The synthetic process is simpler than previously known processes and operates at a much higher yield.

2. Background Art

The preparation of dimethylgold(III) β-diketonates has been known for many years. There is a synthetic procedure set forth by Brain and Gibson, "The Organic Compounds of Gold. Part VII. Methyl and Ethyl Compounds", J. Chem. Soc., 762 (1939). The process involves the preparation of dimethylmonoiodogold dimer by the reaction of an ethereal solution of methyl magnesium iodide with pyridinotrichlorogold in dry pyridine. The dimethylmonoiodogold dimer is then reacted with thallous acetylacetonate to produce the desired dimethylgoldacetylacetonate. This two step process suffers from the deficiencies that the yield is quite low, in the range of 10–20%, and the presence of any thallium salt resides cause unacceptable contamination for use in semiconductor components.

The trifluoroacetylacetone and the hexafluoroacetylacetone complexes have been prepared in a similar manner as set forth by Komiya and Kochi, "Reversible Linkage Isomerisms of β-Diketonato Ligands. Oxygen-Bonded and Carbon-Bonded Structures in Gold(III) Acetylacetone Complexes Induced by Phosphine", JACS, vol. 99, 3696 (1977). These complexes were found to be unusually volatile, being readily sublimed or evaporated at atmospheric pressure even at room temperature. Thus it can be seen that such complexes may be useful in various metallization processes in the manufacture and repair of semiconductor components.

Following the literature procedure, tetrahaloauric acid (viz., tetrabromoauric acid) was precipitated from an aqueous solution with pyridine. The resulting trihalogold(III) pyridyl complex (viz., tribromogold(III) pyridyl complex) was isolated as a stable solid. This material was dried, dissolved in dry pyridine, and heated to 80° C. to form a di-pyridylgold(III) complex. To the cooled solution of this di-pyridyl complex in pyridine was added a freshly prepared Gringard reagent, preferably MeMgI. The product of this reaction (dimethylgold(III) iodide dimer) was isolated by a tedious several step procedure. This material was recovered in low yield (20%). (This dimethylgold(III) iodide dimer is reported to be explosive, subject to detonation upon grinding.) The purified dimer product was reacted with the thallium salt of trifluoroacetylacetone and provided a yield on this step of 80%. The overall yield on the process was about 16%. The potassium salt of trifluoroacetylacetone may also be used.

SUMMARY OF THE INVENTION

The invention of this application is to a process for the synthesis of dialkylgold(III) β-diketonates comprising the steps of reacting gold trihalide with an alkyl lithium in anhydrous ether, adding a β-diketone to the reaction mixture, and recovering the dialkylgold(III) β-diketonate. The synthesized compounds are particularly useful in chemical vapor deposition and laser-induced metallization of semiconductor components. The synthetic process is simpler than previously known processes and operates at a much higher yield.

DETAILED DESCRIPTION

The present invention provides a two-step, one-pot process for the synthesis of dialkylgold(III) β-diketonates. The first step comprises the addition of an alkyl lithium to gold trihalide to form a trialkylgold intermediate. It has been found that it is undesirable to do a separate work-up to isolate this trialkylgold intermediate because it is unstable, decomposing below room temperature. The second step comprises the addition of a β-diketone to the reaction mixture to form the desired dialkylgold(III) β-diketonate. The alkyl lithium compounds include methyl lithium, ethyl lithium, n-propyl lithium, i-propyl lithium, n-butyl lithium, i-butyl lithium and t-butyl lithium. Methyl lithium is most preferred because it forms the most stable gold complexes. As the alkyl group gets larger the resulting complexes exhibit lower volatility and are more unstable. The gold trihalides include $AuBr_3$, $AuCl_3$, and $AuI_3$. Gold tribromide is most preferred. The β-diketones useful in the synthesis of the invention include acetylacetone, 1,1,1-trifluoroacetylacetone, and 1,1,1,5,5,5-hexafluoroacetylacetone. Other β-diketones, both alkyl and aryl substituted, may be effectively used in the synthetic process of the present invention. The use of trifluoroacetylacetone leads to the most preferred end products (dialkylgold trifluoroacetylacetonates) which are useful in laser induced metallization of semiconductor components.

EXAMPLE

Synthesis of dimethylgold trifluoroacetylacetonate

A three-necked round-bottom flask equipped with a cooling bath, mechanical stirrer, thermocouple temperature sensor, nitrogen inlet, and dropping funnel was carefully flushed with nitrogen. The flask was charged with 120.0 grams of gold tribromide (274.8 mmol) to which 1.9 liters of anhydrous (directly from freshly-opened cans) diethyl ether was added. The resultant mixture was a brown slurry which was stirred while Dry Ice and acetone were added to the cooling bath to bring the bath temperature to −80° C. When the internal temperature of the slurry dropped below −60° C., the slurry was deoxygenated by alternately pulling a vacuum (25"Hg) and refilling with nitrogen. This sequence was repeated five times. A solution of methyl lithium in ether (550 mL of 1.50 M $CH_3Li/Et_2O$, 825.0 mmol, 3.00 equiv.) was then charged to the dropping funnel via syringe. When the internal temperature of the reaction mixture reached −80° C., methyl lithium addition was started. The methyl lithium was added slowly over a period of 70 minutes. An initial exotherm was noticable. A small portion (40 mL) of diethyl ether was used to rinse out the dropping funnel. When the methyl lithium addition was completed, the reaction mixture (an almost clear, but dark-brown solution) was allowed to stir at −80° C. for an additional 1 hour, during which time a solution of 63.6 grams of trifluoroacetylacetone (412.5 mmol, 1.50 equiv.) in 135 mL of diethyl ether was charged to the dropping funnel. [The trifluoroacetylacetone, $CF_3COCH_2COCH_3$, was previously distilled under argon at atmospheric pressure (bp 104–6° C.) to give a clear colorless oil. The distilled material was kept refrigerated until use to prevent discoloration.] After the 1-hour stirring period, addition of the trifluoroacetylacetone solution was begun. This solution was added over a period of 25 minutes, while cooling of the reaction was continued. The reaction mixture rapidly became a brown suspension, with traces of metallic gold on the flask walls. After the addition was completed, the reaction mixture was stirred at $-80°$ C. for an additional 2 hours. The reaction was then allowed to slowly warm to room temperature over a period of 2 hours. After an additional 30 minutes stirring at room temperature, the reaction was treated with 15 mL of deionized water, dropwise, to destroy any remaining traces of methyl lithium. Another 235 mL of water was then added. This multiphasic mixture was stirred for 30 minutes. The liquid portions of the reaction were decanted into a separatory funnel and the solids (primarily gold) were washed with a few mL of water and ether and these washings were added to the funnel. The organic phase was separated and washed with five portions of deionized water (200 mL each), dried over anhydrous sodium sulfate, filtered, and carefully stripped on a rotary evaporator. Dimethylgold trifluoroacetylacetonate is rather volatile so that care must be taken in evaporating solutions of this material; a vacuum of 15" of Hg was used, along with a room temperature bath. On the other hand, its thermal-, photo-, and/or oxidative stability appear to be poorer in solution. As a result, solutions should be evaporated as quickly as feasible. The crude product, weighing 89.2 grams, crystallized after the solvent had been removed. The crude material was chromatographed on silica gel. The column (24 cm high ×13 cm diameter, 1500 grams of silica gel) was set up using 10% diethyl ether in pentane. After the crude material was applied to the column (some of it was insoluble), 10% diethyl ether in pentane was used as the elutant. The fractions were monitored by silica gel TLC, using 20% diethyl ether in pentane as the solvent; dimethylgold trifluoroacetylacetonate eluted first ($R_f=0.8-0.9$) with usually a clear break before the next material. The appropriate chromatography fractions were combined and stripped. 60.48 grams of a white crystalline solid having a slight yellowish cast and a melting point of 38°-39° C. were recovered, providing a 57% yield.

Dimethylgold acetylacetonate was prepared and purified using the synthetic procedures set forth above. The final product was a white crystalline solid with a melting point of 82° C. The material was obtained in about a 30% yield.

We claim:

1. A process for the synthesis of a dialkylgold(III) β-diketonate comprising the steps of
   (a) reacting a gold trihalide with an alkyl lithium compound in anhydrous ether,
   (b) adding a β-diketone to the reaction mixture, and
   (c) recovering the dialkylgold(III) β-diketonate.

2. The process of claim 1 wherein the gold trihalide is selected from the group consisting of $AuBr_3$, $AuCl_3$, and $AuI_3$.

3. The process of claim 1 wherein the alkyl lithium compound is selected from the group consisting of methyl lithium, ethyl lithium, n-propyl lithium, i-propyl lithium, n-butyl lithium, i-butyl lithium, and t-butyl lithium.

4. The process of claim 1 wherein the β-diketone is an alkyl or aryl substituted β-diketone.

5. The process of claim 4 wherein the β-diketone is selected from the group consisting of acetylacetone, trifluoroacetylacetone, and hexafluoroacetylacetone.

* * * * *